United States Patent [19]

Kasperek et al.

[11] 4,263,098

[45] Apr. 21, 1981

[54] RADIATION MEASURING PROCESS FOR DETERMINING THE CONCENTRATION OF FAT IN MEATS

[75] Inventors: Karl Kasperek, Düren; Peter Glozbach, Jülich, both of Fed. Rep. of Germany

[73] Assignee: Kernforschungsanlage Jüιξζ ≈βιιβξζαδ σ πβξζαρθ ~αδρεə Jülich, Fed. Rep. of Germany

[21] Appl. No.: 78,819

[22] Filed: Sep. 25, 1979

[51] Int. Cl.³ .................... G01N 33/12; G01N 23/22; G01N 23/222
[52] U.S. Cl. .................... 176/10; 23/230 R; 23/230.3; 250/303; 250/308; 250/358 R; 250/492 R
[58] Field of Search ................ 23/230.3, 230 R; 250/358 R, 492 R, 303, 308

[56] References Cited

U.S. PATENT DOCUMENTS

| | | | |
|---|---|---|---|
| 2,992,332 | 7/1961 | Madigan | 250/358 |
| 3,299,268 | 1/1967 | Muto | 250/83.6 R |
| 3,723,732 | 3/1973 | Larson | 250/106.1 |
| 4,168,431 | 9/1979 | Henriksen | 250/358 R |
| 4,171,164 | 10/1979 | Groves | 250/358 R |

OTHER PUBLICATIONS

"Concise Encyclopaedia of Nuclear Energy", p. 594, Interscience, New York, 1962.

Primary Examiner—Sidney Marantz
Attorney, Agent, or Firm—Karl F. Ross

[57] ABSTRACT

A method of determining the concentration of a substance containing a component capable of induced γ radiation upon irradiation in a neutron flux, especially for the determination of the concentration of fats in meat, in which the body is subjected to the neutron flux, especially from a Cf-252 source, and the induced γ radiation is discriminated and analyzed, especially for the γ radiation at 1.26 MeV, 2.23 MeV and/or 5.3 MeV.

4 Claims, 1 Drawing Figure

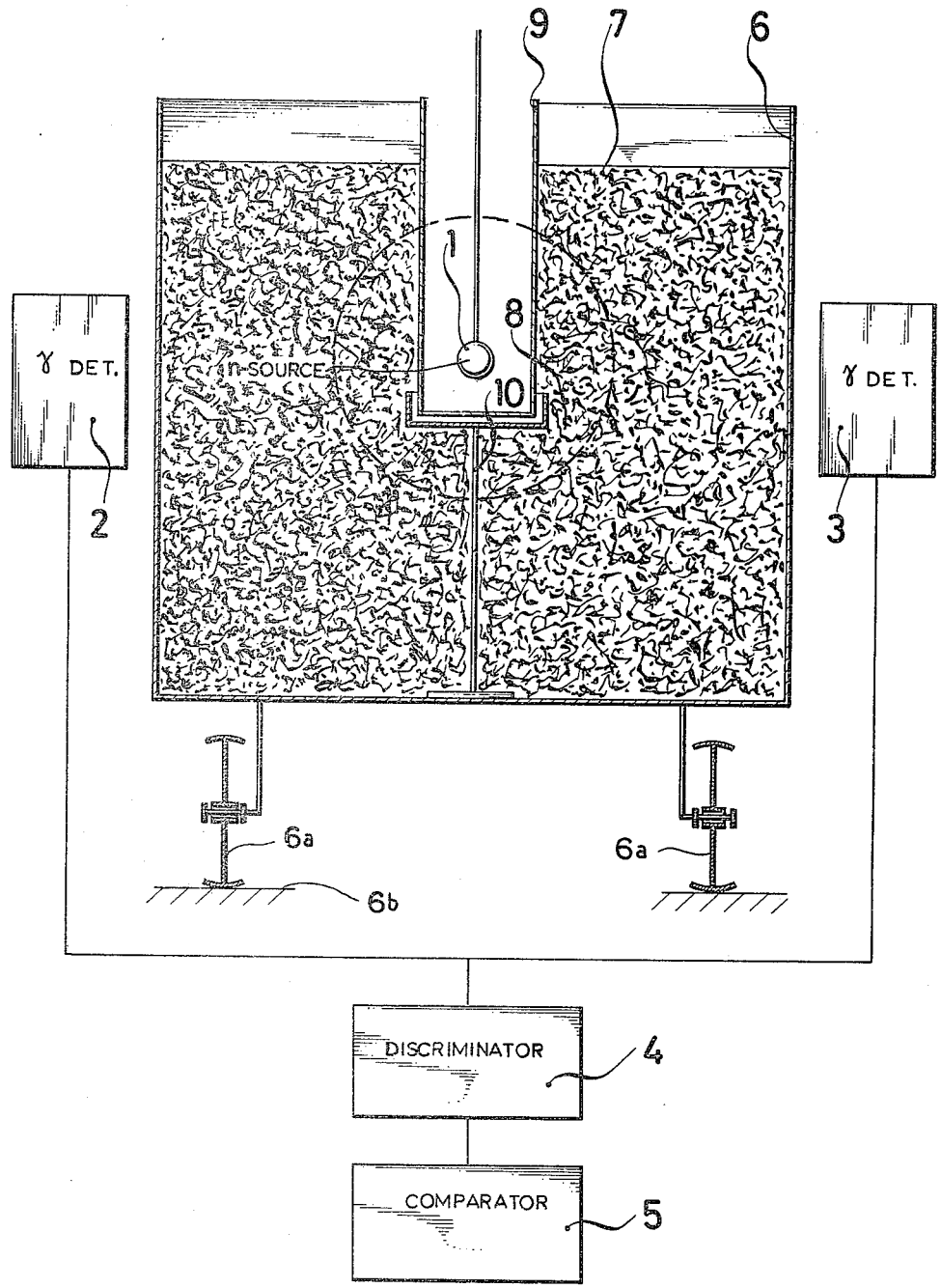

RADIATION MEASURING PROCESS FOR DETERMINING THE CONCENTRATION OF FAT IN MEATS

FIELD OF THE INVENTION

The present invention relates to a method of determining the concentration of at least one substance, containing at least one component undergoing (n,γ) reactions upon neutron irradiation, by the measurement of the promptly emitted γ radiation, in a body.

More particularly, the invention making use of the (n,γ) reaction for determining concentrations of organic components is of advantage, for example, in measuring the fat content of a mass of meat. As in most concentration-measurement cases, a sample of the body to be evaluated is irradiated with neutrons, the induced radiation is measured, the measured γ radiation is discriminated and the concentration calculated on the basis of the discriminated measured values. Results are obtained for determining the fat content of meats when the discriminated γ of an energy of 1.26 MeV is used and negligible quantities of carbohydrates, nucleic acids and trace elements are present as is the case with meats and where the water content is constant or assumed to be constant.

BACKGROUND OF THE INVENTION

Monitoring the fat content of meats, e.g. butchered meat products and wursts, requires a rapid measurement of the fat content in a manner which will be least detrimental to the product and highly accurate. Earlier measurement systems have involved determination of specific gravity and the use of chemical analytical processes or X-ray absorption, the chemical techniques involving an infrared drying and like techniques which are generally time-consuming and only intermittently effective, i.e. cannot be carried out continuously.

In other words, by conventional processes it is not possible to obtain a rapid and continuous indication of the fat content. While the X-ray absorption approach does not damage the product, it must be carried out upon samples and specimens removed from the product so that the production process must be interrupted by the sampling requirement. In all cases, the specimens or samples are small, usually on the order of grams, except in the case of specific gravity measurements, in which case units of about 17 kg are measured.

OBJECTS OF THE INVENTION

It is the principal object of the present invention to provide an improved process for a practically immediate and continuous determination of fat in meat products which can be applicable to a large portion of the product rather than merely small samples thereof.

Another object of the invention is to provide a process for the determination of fat concentration which avoids the disadvantages of earlier systems.

SUMMARY OF THE INVENTION

These objects and others which will be apparent hereinafter are attained, in accordance with the present invention, by a method which involves the use of an (n,γ) process for the determination of fats in meat and which provides, especially in the case of discriminated spontaneous γ radiation measurement, an immediate indication of the concentration based upon a calibrating or characteristic curve. While the (n,γ) process has been used for ore prospecting (see J. I. Tombka et al., Nucl. Instr. and Meth., 87, 1970, pp. 37–43) and for petroleum (see British Pat. No. 1,446,692), these methods have either only determined inorganic components or organic components in an inorganic material and have not heretofore been described, to the best of our knowledge, as being capable of distinguishing organic materials from one another.

Presumably since organic materials are almost invariably made of the elements carbon, hydrogen, nitrogen and oxygen, it has been felt that practically all of the organic components of a system containing similar elements would act in the same way upon irradiation by neutrons.

Surprisingly, we have found that it is possible to establish a characteristic curve or calibrating curve for neutron-irradiated fat-containing means products which will afford an almost accurate measurement of the fat concentration in the meat.

The neutron irradiation reactions which predominate are the following (indicating special γ-lines):

| | | | | |
|---|---|---|---|---|
| C-12 | (n, γ1) | C-13, | especially | $\gamma 1 = 1.26$ MeV |
| H-1 | (n, γ2) | H-2, | especially | $\gamma 2 = 2.23$ MeV |
| N-14 | (n, γ3) | N-15, | especially | $\gamma 3 = 5.3$ MeV |

Other characteristic γ emissions are at, for example, 4.95 MeV for carbon and 1.88 MeV for nitrogen.

These reactions can result from irradiation with thermal neutrons, although for greater precision fast neutrons showing longer range can be used as well and, in general, it has been found that optimum results are obtained when a range of neutron energies is used, for example, the neutron spectrum from Cf-252.

From the following table, the important components of bone-free meat, namely, water, protein and fat, can be readily distinguished by reason of their differences in elemental makeup, especially if the carbohydrates, nucleic acids and trace elements are present only in small amounts:

| Components | Usual % proportion in bone-free meat | Percentage elemental composition | Percentage of the element in the respective meat component |
|---|---|---|---|
| Water (W) | 60% | 11% H | 6.6% $H_W$ |
| | | 89% O | 53.4% $O_W$ |
| Protein (E) (albumin) | 20% | 16% N | 3.2% $N_E$ |
| | | 43% C | 8.6% $C_E$ |
| | | 41% O,H, [P,S] | 8.2% $O_E, H_E$ [P,S] |
| Fat (F) | 15% | 76% C | 11.4% $C_F$ |
| | | 24% O,H | 3.6% $O_F, H_F$ |
| Carbohydrates | 1% | 40% C | 0.4% C |
| | | 60% O,H | 0.6% O,H |
| Nucleic acids | 1% | 40% C | 0.4% C |
| | | 60% O,H,N,P,S | 0.6% O,H,N,P,S |
| Electrolytes and trace elements | 3% | | 3% |
| | 100% | | 100% |

As can be seen from the table, in which the carbon content attributed to the fat is 76% while that attributed to the protein is only 43%, it is possible to evaluate the fat content based upon the spontaneous γ emission at 1.26 MeV to establish the characteristic curve for fat content. Preferably, however, a three-channel analyzer is provided to measure the discriminated γ radiation levels at C (1.26 MeV), H (2.23 MeV) and N (5.3 MeV).

The fat content can be determined in each case by the relationships:

$$\% \text{ Fat} \approx 1.32 \ [\% \text{ C total} - \% \text{ C protein}]$$
$$\approx 1.32 \ [\% \text{ C total} - 2.7\% \text{ N protein}]$$
$$\approx 1.32 \ [\% \text{ C total} - 3.6\% \text{ N protein}]$$
$$\approx 1.32 \ F_C \text{ Act (C)} - 3.6\% \ F_N \text{ Act (N)}.$$

In these equations, $F_C$ and $F_N$ are factors for the conversion of the corresponding C and N measurements into the respective concentrations and are simplified by assuming that the nitrogen derives only from the protein. The water content is considered by the equation:

$$\% \ H_2O = K \cdot [H \text{ total} - 0.44 \ N_E - 0.15 \ C_F]$$

which takes into consideration the necessary corrections based upon the fact that a higher water content gives a reduced total carbon which means reduced fat content as well.

In addition, the invention additionally can make use of an activation radiation, e.g.:

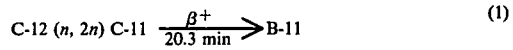  (1)

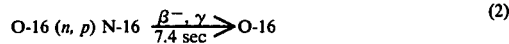  (2)

and supplementary measuring of retarded (delayed) γ-emissions.

BRIEF DESCRIPTION OF THE DRAWING

The above and other objects, features and advantages of the present invention will become more readily apparent from the following description, reference being made to the accompanying drawing, the sole FIGURE of which is a diagrammatic illustration of an apparatus for practicing the invention.

SPECIFIC DESCRIPTION

In the drawing we have shown a standard-volume carriage 6 which is formed with a longitudinal trough 9 (with open front walls) and which is displaceable on wheels 6a along a track represented at 6b to carry a mass of meat past a neutron source which is suspended from an upper location above the track so that the neutron source lies within the trough as the trough and wagon are displaced continuously past the neutron source.

In the preferred embodiment of the invention, the neutron source, which can be one microgram of Cf-252, is disposed between two detectors 2, 3 flanking the path and connected to a three-channel analyzer 4 forming an energy discriminator for γ radiation induced in the meat by the neutron irradiation. A calculator or microcomputer 5 is connected to the analyzer to provide a direct readout of the fat concentration, having been programmed with the fat concentration characteristic curve previously.

The positioning of the source 1 within the upwardly open longitudinally throughgoing trough 9 so that the neutron source is disposed within the depth of the body meat content in the carriage, eliminates measurement errors which may result from differences in the filling height of the wagon, the region from which the measurement derives being represented by broken line at 8.

The trough 9 may be carried by a pedestal or support 10 on the bottom of the carriage for simplicity of construction. Naturally, a downwardly open trough can also be provided with the neutron source projecting upwardly into this trough. In still another alternative, at a predetermined location in the meat-processing line, a neutron source can be provided which can be lowered into a body of meat which is disposed between two fixed detectors. In this case, the neutron source 1 can be surrounded by a sleeve and can be simply inserted into the wagon briefly and removed therefrom or can be permitted to remain for a given time interval as the wagon moves past so as to traverse the full length of the mass of the meat.

The radiation detectors can be scintillation counters with appropriate discriminating foils or circuitry so that only the γ radiation of the desired energy is counted.

With a one microgram Cf-252 source, the neutron flux is $10^6$ to $10^7$ neutrons per second and hence there is little danger that enduring activation of the meat will occur. The highest induced radioactivity of a half life of more than one minute appears to arise from Cl-38 with an activity of about 2 nC/kg which is about 1/50th the activity of the K-40 naturally present. The half life of the Cl-38 is only 37 minutes so that after six hours only about 1/1000th and after another six hours only about 1/1,000,000 of the induced activity remains.

While the specific example to which the principles of the invention have been applied is for the determination of the fat concentration in meat, the principles are also applicable to the water content or the protein content in meat products or even in living organisms.

We claim:

1. A method of determining the fat concentration in a mass of meat, said method comprising the steps of:
   subjecting said mass of meat to a neutron flux sufficient to induce (n,γ) reactions in the mass of meat and prompt γ emission therefrom;
   measuring the induced prompt γ radiation emitted for at least one selected γ energy; and
   comparing the measured values at said selected γ energy with a standard representing concentration of fat in said mass of meat, thereby obtaining a measurement of said concentration.

2. The method defined in claim 1 wherein the γ radiation which is measured is γ radiation with a characteristic energy of 1.26 MeV, when determining fat in meat containing negligible quantities of carbohydrates, nucleic acids and trace elements with a substantially constant water content.

3. The method defined in claim 2, further comprising measuring the discriminated γ radiation at 2.23 MeV and 5.3 MeV.

4. The method defined in claim 3 wherein the neutron flux derives from a Cf-252 neutron source.

* * * * *